(12) United States Patent
Ganter et al.

(10) Patent No.: US 9,844,388 B2
(45) Date of Patent: *Dec. 19, 2017

(54) SURGICAL GRIPPING FORCEPS

(75) Inventors: Hans Ganter, Tuttlingen (DE); Josef Reinauer, Sigmaringen (DE)

(73) Assignee: KARL STORZ GMBH & CO. KG, Tuttlingen (DE)

( * ) Notice: Subject to any disclaimer, the term of this patent is extended or adjusted under 35 U.S.C. 154(b) by 1173 days.

This patent is subject to a terminal disclaimer.

(21) Appl. No.: 12/304,365

(22) PCT Filed: Jun. 14, 2007

(86) PCT No.: PCT/EP2007/005245
§ 371 (c)(1),
(2), (4) Date: Mar. 3, 2009

(87) PCT Pub. No.: WO2007/144172
PCT Pub. Date: Dec. 21, 2007

(65) Prior Publication Data
US 2009/0259248 A1 Oct. 15, 2009

(30) Foreign Application Priority Data
Jun. 14, 2006 (DE) .................. 10 2006 028 001

(51) Int. Cl.
*A61B 17/29* (2006.01)
(52) U.S. Cl.
CPC ........ *A61B 17/29* (2013.01); *A61B 2017/294* (2013.01); *A61B 2017/2933* (2013.01); *A61B 2017/2947* (2013.01)
(58) Field of Classification Search
CPC . A61B 10/06; A61B 17/29; A61B 2017/2939; A61B 18/1445;

(Continued)

(56) References Cited

U.S. PATENT DOCUMENTS 3,895,636 A * 7/1975 Schmidt ................. A61B 10/06
30/188
4,038,987 A * 8/1977 Komiya ........................ 606/142
(Continued)

FOREIGN PATENT DOCUMENTS

DE 201 20 249 3/2002
EP 0 623 316 A1 4/1994
EP 0623316 A1 * 11/1994

OTHER PUBLICATIONS

International Search Report and Written Opinion, 6 pages, PCT No. PCT/EP2007/005245, dated Sep. 25, 2007.
(Continued)

*Primary Examiner* — Anh Dang
*Assistant Examiner* — Erin Colello
(74) *Attorney, Agent, or Firm* — Andrew F. Young, Esq.; Lackenbach Siegel, LLP

(57) ABSTRACT

The invention relates to surgical gripping forceps with two gripping jaws movable relative to a main body, with each gripping jaw having a stationary pivot axis relative to the main body, and a lever arm, and with the lever arms being articulated via at least one push element. Each gripping jaw has its own pivot axis. The distance between the individual pivot axis and the midline of the main body is at least greater than 38% of the maximum width of the main body or the maximum diameter of the main body. The present invention also provides microsurgical gripping forceps that a substantial clamping force between the gripping jaws with customary force for actuating the forceps.

6 Claims, 4 Drawing Sheets

(58) Field of Classification Search
CPC .... A61B 2017/2936; A61B 2017/2926; A61B 2017/2932; A61B 2017/2933; A61B 2017/2934; A61B 2017/2941; A61B 18/1442; A61B 2017/294; A61B 2017/2947; A61B 17/3201; A61B 18/085; A61B 2018/1457; A61B 2018/146; A61B 17/1606; A61B 17/1608; A61B 17/32; A61B 17/320016
USPC ....... 606/205, 207, 208, 206, 209, 210, 211, 606/174, 51, 52
See application file for complete search history.

(56) References Cited

U.S. PATENT DOCUMENTS

| | | | |
|---|---|---|---|
| 4,887,612 A * | 12/1989 | Esser | A61B 10/06 294/116 |
| 5,275,615 A | 1/1994 | Rose | |
| 5,290,309 A | 3/1994 | Kothe | |
| 5,342,390 A | 8/1994 | Slater et al. | |
| 5,373,854 A | 12/1994 | Kolozsi | |
| 5,569,299 A | 10/1996 | Dill et al. | |
| 5,700,275 A * | 12/1997 | Bell | A61B 17/2909 606/206 |
| 5,749,893 A | 5/1998 | Vidal et al. | |
| 5,762,613 A * | 6/1998 | Sutton et al. | 600/564 |
| 5,779,648 A * | 7/1998 | Banik et al. | 600/567 |
| 5,843,000 A * | 12/1998 | Nishioka et al. | 600/566 |
| 5,964,779 A * | 10/1999 | Mayenberger | A61B 17/29 600/564 |
| 6,019,780 A * | 2/2000 | Lombardo et al. | 606/207 |
| 6,083,150 A * | 7/2000 | Aznoian | A61B 10/06 600/564 |
| 6,086,606 A * | 7/2000 | Knodel | A61B 17/29 606/174 |
| 6,129,683 A * | 10/2000 | Sutton et al. | 600/564 |
| 6,159,162 A * | 12/2000 | Kostylev et al. | 600/564 |
| 6,394,998 B1 * | 5/2002 | Wallace et al. | 606/1 |
| 6,451,018 B1 * | 9/2002 | Lands et al. | 606/50 |
| 6,767,349 B2 * | 7/2004 | Ouchi | 606/51 |
| 6,818,007 B1 * | 11/2004 | Dampney | A61B 17/29 606/205 |
| 6,964,662 B2 * | 11/2005 | Kidooka | 606/52 |
| 6,969,389 B2 * | 11/2005 | Kidooka | 606/51 |
| 7,762,960 B2 * | 7/2010 | Timberlake | A61B 10/06 600/564 |
| 7,951,165 B2 * | 5/2011 | Golden et al. | 606/205 |
| 2002/0143358 A1 * | 10/2002 | Domingo | A61M 29/02 606/190 |
| 2003/0135204 A1 * | 7/2003 | Lee et al. | 606/1 |
| 2004/0044363 A1 * | 3/2004 | Fowler | A61B 17/1285 606/205 |
| 2005/0021002 A1 * | 1/2005 | Deckman et al. | 604/527 |
| 2005/0043758 A1 * | 2/2005 | Golden et al. | 606/206 |

OTHER PUBLICATIONS

International Publication No. WO 02/064020 published Aug. 22, 2002 (6 pages).
Getman U.S. Appl. No. DE 10 2006 028 001 filed Jun. 14, 2006, Office Action, 5 pages (full translation).
German Application Serial No. 07 726 009.9 dated Feb. 23, 2011 Office Action, 6 pages. (English translation).

* cited by examiner

Fig. 1
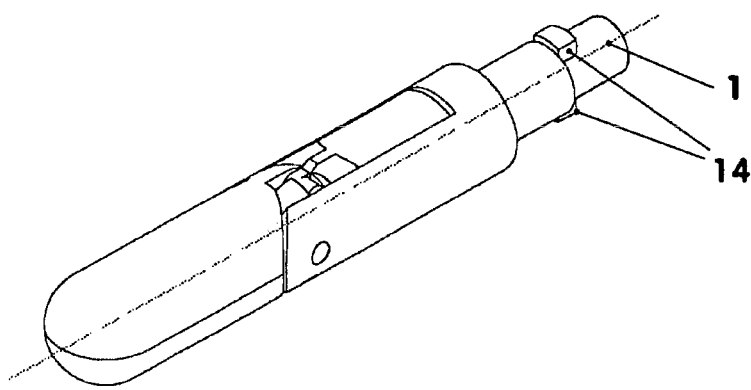
Fig. 2
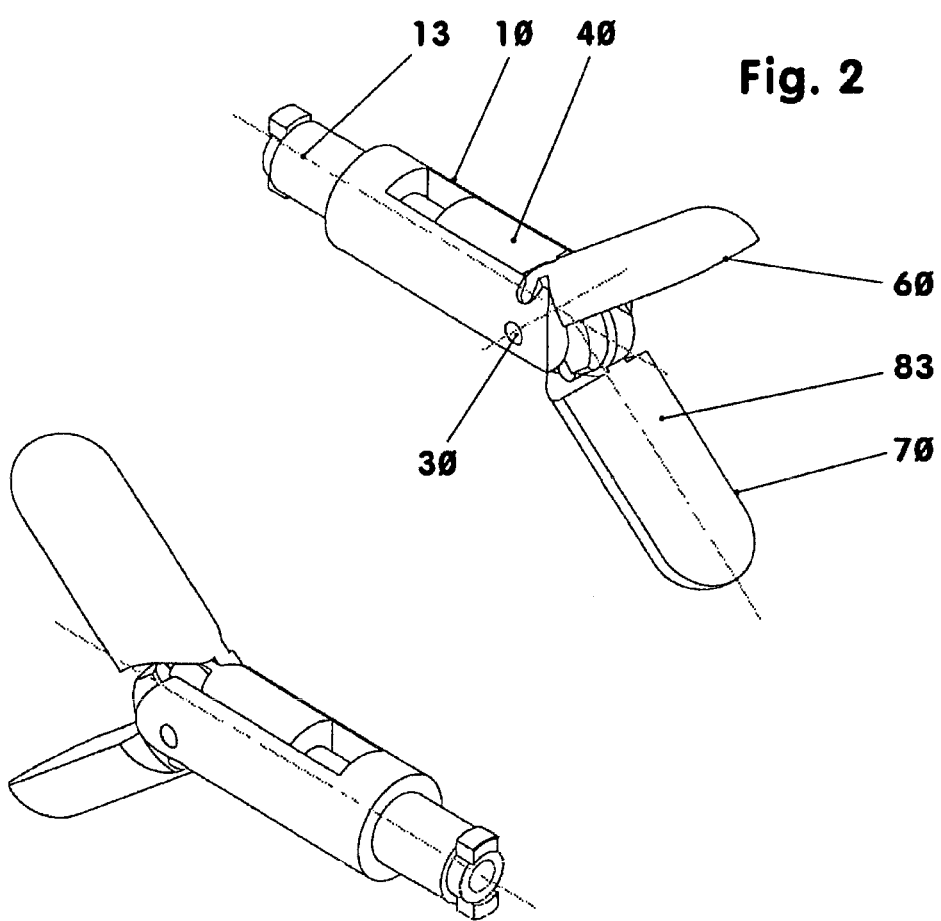
Fig. 3

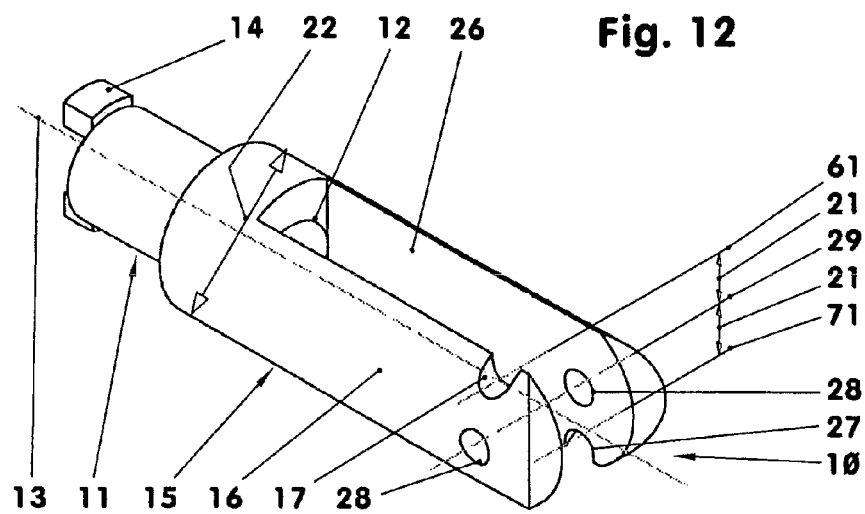
Fig. 12
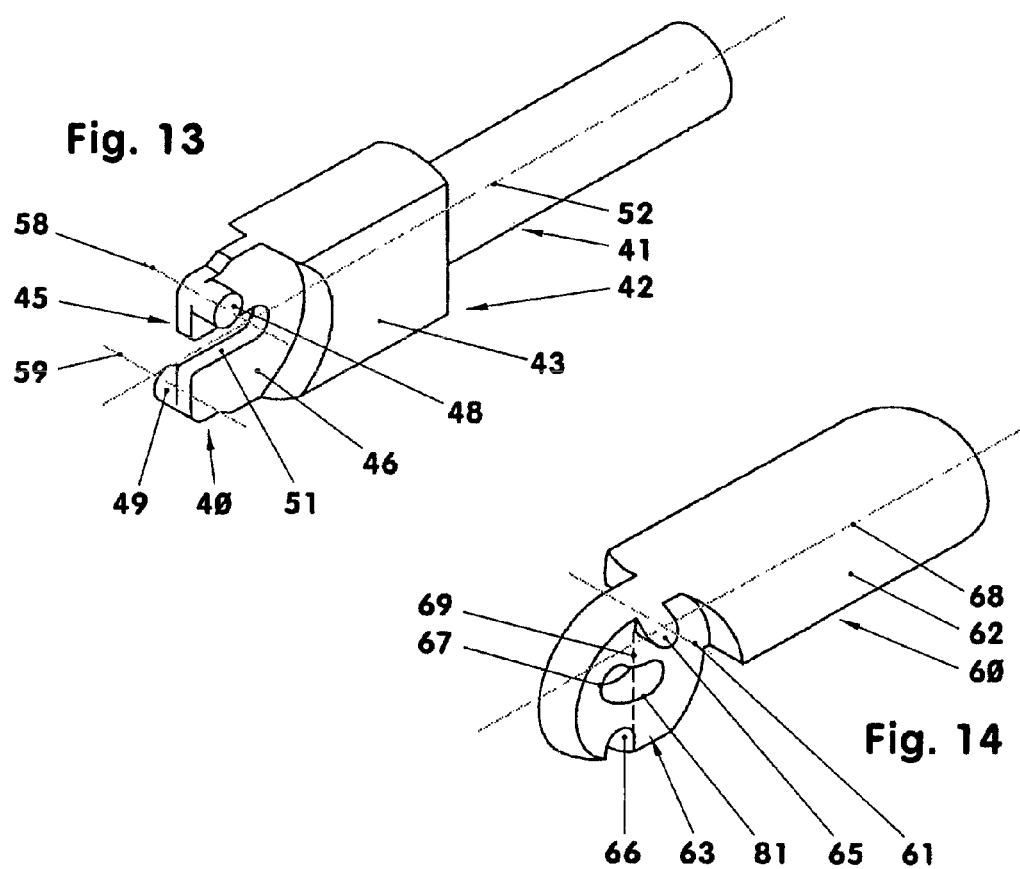
Fig. 13
Fig. 14

SURGICAL GRIPPING FORCEPS

CROSS REFERENCE TO RELATED APPLICATIONS

This application claims priority from Ser. No. PCT/EP2007/005245 filed Jun. 14, 2007, the entire contents of which are herein incorporated by reference. This application in turn claims priority from DE App. Ser. No. 10 2006 028 001.6 filed on Jun. 14, 2006.

FIGURE SELECTED FOR PUBLICATION

FIG. 2

BACKGROUND OF THE INVENTION

1. Field of the Invention

The present invention relates to surgical gripping forceps with two gripping jaws movable relative to a main body. More specifically, the present invention relates to surgical gripping forceps with movable gripping jaws, with each gripping jaw having a stationary pivot axis relative to the main body, and a lever arm, and with the lever arms being articulated via at least one push element.

2. Description of the Related Art

The related art involves gripping forceps known from, for example, U.S. Pat. No. 5,342,390. As noted in '390, the gripping jaws of these forceps are disposed on a jointly used pivot pin. The pivot pin intersects the midline of the main body of the forceps. In this way, the lever arms molded at the gripping jaws, through which gripping jaws are moved, can inevitably be developed relatively short. Also, a separate push element acts on each lever arm of the gripping jaws.

What is not appreciated by the prior art is the need for substantial claming force in a small size while allowing for customary or minimized actuating force.

ASPECTS AND SUMMARY OF THE INVENTION

The present invention is based on the now-recognized problem of developing surgical gripping forceps that allow a substantial clamping force with a customary force for actuating the forceps. Now appreciated by the inventors, the goal is to realize a small number of components with a small structural size of the forceps.

An object of the present invention is to provide surgical gripping forceps wherein each gripping jaw has its own pivot axis. The distance between the individual pivot axis and the midline of the main body is greater than about 38% of the maximum width of the main body or the maximum diameter of the main body.

Laparoscopic surgery requires special instruments. What all instruments have in common is the miniaturization, which is why laparoscopic surgery is also called endoscopic microsurgery. The instruments are inserted into the abdomen through long sleeves that generally have a diameter of between four to 12 millimeters, usually via Torkar sleeves, and they are operated manually outside of the abdominal cavity.

Microsurgery requires micro gripping instruments for the preparation as well as macro instruments for the extraction of resected organs. Various gripping instruments with a diameter of three, five or ten millimeters are available. There are atraumatic forceps as well as toothed forceps. They have gripping jaws that are pointed or wide, micro or macro. Some of the gripping instruments also have locking mechanisms.

The gripping jaws must be designed to be operated simply and safely. This includes a large manual force multiplication by the gripping forceps mechanism. It is also especially advantageous if the gripping forceps, i.e. the part that protrudes in the abdomen from the front of the Torkar sleeve, has as few parts as possible. Fewer parts always also means fewer joints for movement. This reduces the risk of injury and facilitates the disinfection of the gripping forceps. Logically, the latter applies only if the appropriate forceps are not a disposable device.

The present invention relates to a surgical gripping forceps with two gripping jaws movable relative to a main body, with each gripping jaw having a stationary pivot axis relative to the main body, and a lever arm, and with the lever arms being articulated via at least one push element. Each gripping jaw has its own pivot axis. The distance between the individual pivot axis and the midline of the main body is at least greater than 38% of the maximum width of the main body or the maximum diameter of the main body. The present invention also provides microsurgical gripping forceps that a substantial clamping force between the gripping jaws with customary force for actuating the forceps.

The above, and other aspects, features and advantages of the present invention will become apparent from the following description read in conduction with the accompanying drawings, in which like reference numerals designate the same elements.

BRIEF DESCRIPTION OF THE DRAWINGS

FIG. 1 is a perspective view of an embodiment of the present invention for gripping forceps shown in a closed view.

FIG. 2 is an opposite side perspective view of FIG. 1 with the forceps open.

FIG. 3 is a rear perspective view of the embodiment in FIG. 2.

FIG. 12 is a perspective view of a main body element of the present invention.

FIG. 13 is a perspective view of a push element of the present invention.

FIG. 14 is a perspective view of a gripping jaw element of the present invention.

DETAILED DESCRIPTION OF THE PREFERRED EMBODIMENTS

Figure 4:
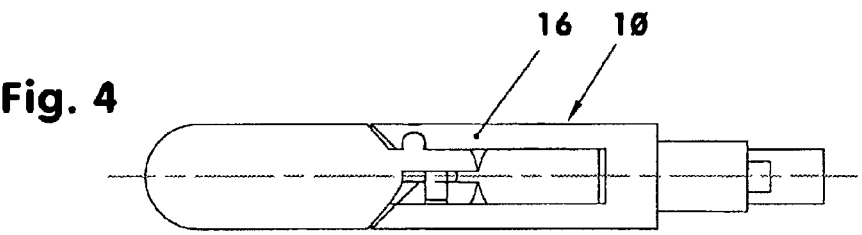
FIG. 4 is a top plan view of the embodiment in FIG. 1 in a closed position.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

Referring now to FIGS. 1-3, surgical gripping forceps 1 of the present invention are shown in closed and open representations. The gripping forceps comprise a main body 10, a push element 40, two gripping jaws 60, 70 and a guide pin 30.

The main body 10 (further noted in FIG. 12) includes a tube section 11 and a fork section 15. The tube section 11 has a boring 12 in which the push element 40 is guided. Two opposing adapter elements 14 are molded at the back end of said push element. Via adapter elements 14, the main body 10 is removably attached at a housing tube (not shown convenience), for example by means of a quarter-turn fastener mechanism.

Fork section 15 has two fork arms 16, 26 that are arranged at the tube section 11, as shown. The outer walls of the fork arms 16, 26 are parts of a cylinder jacket, for example. The diameter of said cylinder is the main body diameter 22. In the embodiment, it is 4.8 mm. The interior walls of the fork arms 16, 26 are planes that are located as parallel opposites. The distance of the planes, for example, corresponds to the interior diameter of the boring 12. At their front ends, fork arms 16, 26 have a respective borings 28, 28. The borings 28, 28, which are in true alignment, have a designated midline 29 that perpendicularly intersects with the midline 13 of the main body 10, as shown graphically.

Each front fork arm 16 (see FIG. 12) has above the boring 28 a recess 17 that is U-shaped, as a groove, for example. The base of the recess partially has the surface area of a cylinder jacket. The center of the cylinder jacket is an upper pivot axis 61. The rear fork arm 26 has a comparable recess 27. The latter is orientated downward here and in part encloses a lower pivot axis 71. The pivot axes 61, 71 and the midline 29 of the borings 28 are located on one plane. This plane is aligned normally relative to the midline 13 of the main body 10.

Referring additionally now to FIG. 13, which depicts the push element 40. Push element 40 includes a push pin section 41, a guide section 42 and a bearing section 45. The push pin section 41, which accommodates the push element 40 in the main body 10, has a cylindrical form. At its free end, the push pin section has a tapped hole, if applicable. In the latter, the actuating rod guided in the housing tube of the forceps is then removably fastened. The tapped hole, the housing tube and the actuating rod are not shown in the figures.

Push pin section 41 is followed by the guide section 42, as shown (see also FIG. 13). The latter has at least approximately the form of a cuboid with two planar, parallel facing side surface areas 43 (as shown). During use, with the assembled gripping forceps, these side surface areas 43 bear against the interior walls of the fork arms 16, 26 of the main body 10, where they act as rotation prevention. The bent partial cylinder areas that border the side surface areas 43 at the top and bottom are part of a cylinder that has a diameter corresponding to the diameter of the main body.

Guide section 42 transitions into a bearing section 45. The bearing section 45 corresponds to a thin-walled plate that has two link pins 48, 49 and a guide groove 51. The link pins 48, 49 have opposite parallel midlines 58, 59. Both midlines 58, 59 clamp a plane that is normally positioned relative to the midline 52 of the push element 40. The upper link pin 48 according to (see FIG. 13) is orientated forwardly, whereas the lower pivot pin 49 is aligned backwardly. Both link pins 48, 49 have the same distance relative to the midline 52. The distance between the midlines 58, 59 is more than two-thirds of the main body diameter 22. The link pins 48, 49 have a diameter of 1 mm, for example.

In the center between the link pins 48, 49 is a straight guide groove 51, which is open toward the free end of the bearing section 45. The closed end of the guide groove 51 has a part-cylindrical round corner. The midline of the round corner perpendicularly intersects the midline 52 of the structural component 40.

Referring additionally now to FIG. 14, one of two gripping jaws 60 is detailed in perspective view. In the spatial relationship to the structural components 10 and 40 shown in FIGS. 12 and 13, this is the upper gripping jaw. Gripping jaw 60 is comprised of a jaw section 62 and a pivot area section 63. Jaw section 62 has the form of half of a longitudinally divided cylinder. The diameter of said cylinder corresponds to the main body diameter 22. The front free end of the jaw section 62 is rounded. The round corner radius corresponds to half of the main body diameter 22.

The at least approximately circular disk-shaped pivot area section 63 runs in the front half of the gripping jaw 60, i.e., the rear planar area of the pivot area section 63—which contacts a bearing surface area 46 of the bearing section 45 of the push element 40—is on a plane that is removed from the plane of the structural component center by half the width of the bearing section 45. The structural component midline 68 runs in said center plane. Also on the structural component midline 68 is the atraumatic jaw gripping surface area 83, which is planar here (see FIG. 2).

In the upper area, the pivot area section 63 has a forward orientated pivot pin 65. The pivot pin 65, which has a midline 61, has at least toward the bottom a cylindrical outer contour. There is a sickle shaped guide recess 67 below the pivot pin 65. The bending radius of the guide recess 67 has a midpoint that is on the midline 61 of the pivot pin 65. Consequently, the guide recess 67 has at least one edge 81 shaped like the arc of a circle, and the midpoint of said edge is also on the midline 61. Below the guide recess 67, a pivot link recess 66 is worked into the pivot area section 63 from the bottom. The pivot link recess 66 is a straight groove, for example, and the width of said groove is slightly greater than the diameter of the link pins 48, 49 of the push element 40. Here too, parts of the base of the recess have the surface area of a cylinder jacket.

As noted in FIG. 14, a dashed auxiliary line 69 has been drawn on the visible planar surface area that bears against the interior wall of the appropriate fork arm 16, 26 of the main body 10 when the gripping forceps are assembled. Auxiliary line 69 is furthermore perpendicular on the plane of the jaw gripping surface area 83. The front jacket line of the pivot pin 65 and the edge of the rear, planar wall of the pivot link recess 66 are on said auxiliary line 69.

The fifth and last structural component of the gripping forceps is the cylindrical guide pin 30, see for example FIG. 2. In the first embodiment, pin 30 has a diameter of approximately 1 mm, and its length is slightly less than the main body diameter 22. Pin 30 sits in the borings 28 of the gripping arms 16, 26, for example by means of a cross press fit.

Preferably, all five parts 10, 30, 40, 60, 70 of the gripping forceps are respectively made of a rust- and acid resistant steel, such as the chromium steel X20Cr13, for example.

Figure 5:
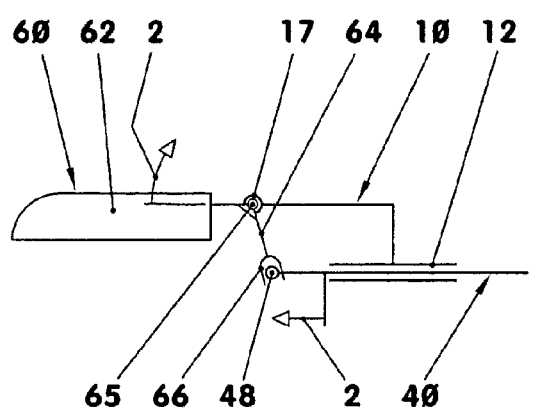
FIG. 5 is a side graphical view of half of a gripping forceps according to the present invention in a closed position noting motion lines.
Figure 6:
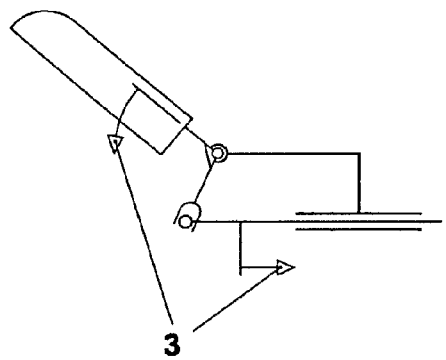
FIG. 6 is a side graphical view of the embodiment in FIG. 5 but in an open position noting motion lines.

Before explaining the cooperation of the forceps components, the operating principle is discussed briefly. Referring now to FIGS. 5 and 6 which pictorially first show the operating principle for only one gripping jaw 60.

As noted in FIGS. 5-8, gripping jaw 60 is a jaw section 62, 72 to which a lever arm 64, 74 with a recess 66, 76 and a pivot pin 65, 75 is fastened. The main body 10 is a boring 12 with a recess 17 arranged thereon. The push element 40 is disposed in the boring 12. It engages with the pivot link recess 66, 76 via a link pin 48.

During operation, to open the gripping jaw 60, the push element 40 is moved toward the left (as shown) in the boring 12. The link pin 48 urgingly acts on the pivot link recess 66 that, together with the lever arm 64 and the jaw section 62, pivots upward in clockwise fashion. While doing so, the pivot pin 65 rotates in the recess 17 of the main body 10 (see for FIG. 6).

Figure 7:
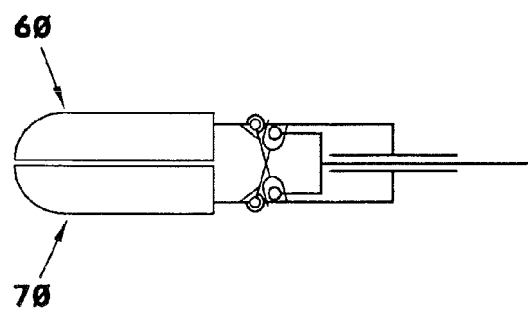
FIG. 7 is a side elevational view of the complete gripping forceps shown in a closed position.
Figure 8:
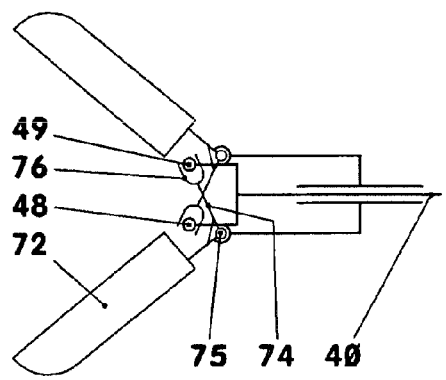
FIG. 8 is the side elevational view in FIG. 7 in an open position.

Referring additionally now to FIGS. 7 and 8 which depict the principle for the entire gripping forceps as noted herein. To that end, the outlines shown in FIGS. 5 and 6 are first reflected downward. Then the original and the mirror image are slid into one another until the gripping jaws 60, 70 are located together, according to FIG. 4. To make do with a straight guide 40 here, both link pins 48, 49 are firmly arranged on a joint push element 40.

Figure 9:
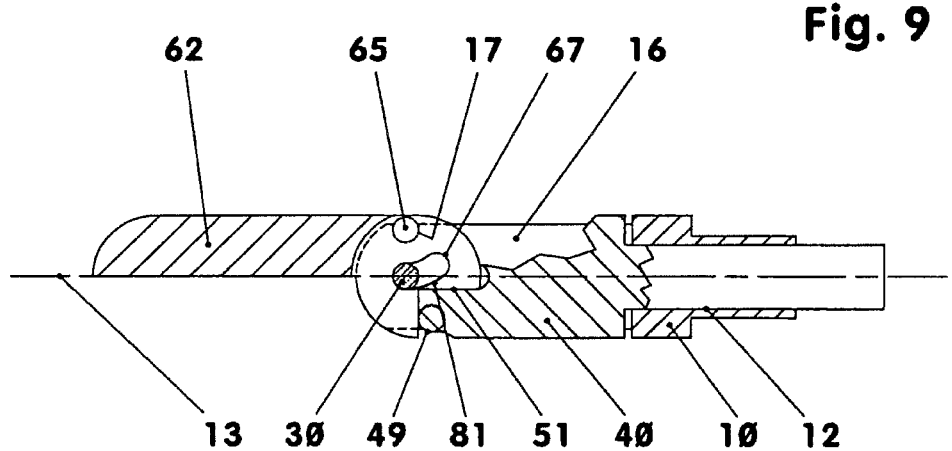
FIG. 9 is a partial cutaway view of a gripping forceps with only one gripping jaw shown in a closed position.

During assembly, the individual parts 10, 30, 40, 60, 70 of the actual gripping forceps, (see FIGS. 12 to 14), are assembled in that the push element 40, with its guide section 42 first, is slid almost completely into the boring 12 of the main body 10. The insertion depth is shown in. FIG. 9. Then the upper gripping jaw 60 is inserted from the top into the gap between the front fork arm 16 and the bearing surface area 46 of the push element 50. In this way, the gripping jaw 60 is in extended position, i.e., its midline 68 runs parallel to the midline 13 of the main body 10 during 5 the insertion process. In the downward movement, the pivot pin 65 of the gripping jaw 60 comes to bear in the recess 17 of the main body 10. Pivot axis 61 is spaced a distance 21 from the midline 29 of boring 28 and pivot axis 71 is spaced by the same distance 21 from the midline 29 of the boring 28, thereby facilitating movement of the law section along directional arrows 2.2. At the same time, the pivot link recess 66 of the gripping jaw 60 is slid over the link pin 49 of the push element 40. The insertion of the gripping jaw 60 is completed as soon as the midline 68 of the gripping jaw 60 corresponds to the midline 13 of the twain body 10. The lower gripping jaw 70 is inserted in the same manner from below.

With this arrangement of structural components, five recesses and/or borings are, at least partially, positioned on top of each other in the pivot area of the gripping forceps. Viewed from outward to inward, these are the two borings 28 of the fork arms 16, 26, the two sickle shaped guide recesses 67, 77 of the gripping jaws 60, 70 and the guide groove 51 of the push element 40. Finally, the guide pin 30 is then inserted through all recesses and affixed; see again FIGS. 1 to 4.

Figure 10:
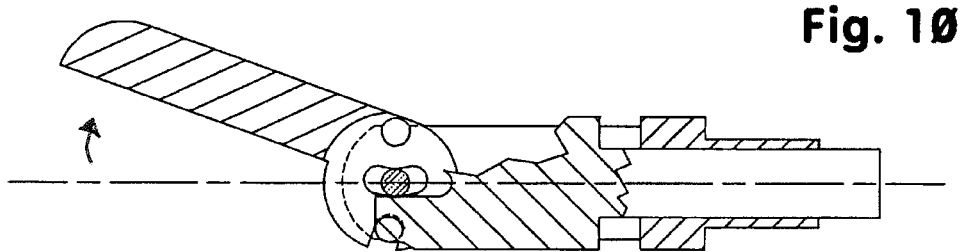
FIG. 10 is a partial cutaway view of a gripping forceps as in FIG. 9 but with the jaw in a half open position.
Figure 11:
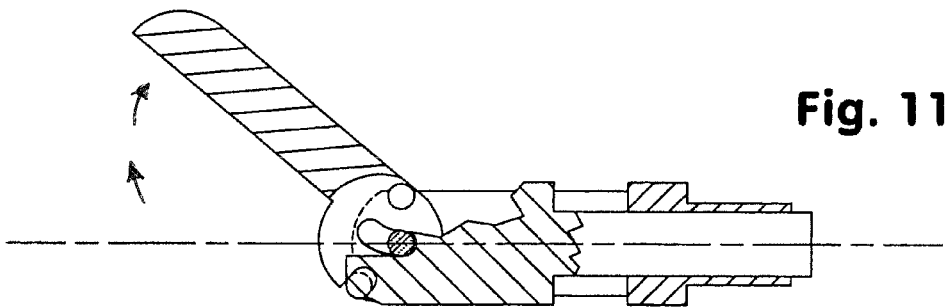
FIG. 11 is a partial cutaway view of a gripping forceps as in FIG. 9 but with the jaw in a completely open position.

The function of the sickle shaped guide recess 67 of the gripping jaw 60, which has not been described so far, is shown now in FIG. 9 to 11. As noted therein, the gripping forceps are shown in longitudinal section without the lower gripping jaw 70. Also, a piece is broken out of the push element 40

The main body 10 accommodates the gripping jaw 60 in the recess 17 and on the guide pin 30. The recess 17, which is open on one side, accommodates the pivot pin 65. To prevent an unintended upward travel of the pivot pin 65 and/or the gripping jaw 60, the guide-pivot link recess 66 bears against the guide pin 30 at least via the edge 81. Because the guide recess 67 bears against the guide pin 30, it is possible to situate the pivot axis 61 of the gripping jaw 30 far away from the midline 13 within the main body 10. This allows a large gripping forceps lever arm.

The novel features that are considered characteristic of the invention are set forth with particularity in the appended claims. In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. A surgical gripping forceps, comprising:
   a first gripping jaw and a second gripping jaw that are movable relative to a main body, wherein said first gripping jaw and said second gripping jaw are diametrically opposed to one another, wherein said first gripping jaw has a first stationary pivot axis relative to said main body and a first lever arm, and said second gripping jaw has a second stationary pivot axis relative to said main body, and a second lever arm, wherein each of said first and second lever arms are articulatable via at least one push element member relative to a defined midline of said main body during a use of said surgical gripping forceps;
   a pivot pin on each of said first and second gripping jaws that projects away from respective ones of said first and second gripping jaws,
   wherein each said pivot pin of respective ones of said first and second gripping jaws extends along said respective ones of said first and second stationary pivot axes of each respective said first and second gripping jaws and forms said respective pivot axis during said use,
   wherein each said pivot pin of said respective first and second gripping jaws that rotates about respective ones of said first and second pivot axes is in a corresponding recess on opposing sides of said main body,
   wherein each respective said first and second pivot axis for said first and second gripping jaws is a distance from said defined midline of said main body that is at least greater than thirty eight percent (38%) of one of a maximum width and a maximum diameter of said main body, and wherein said first stationary pivot axis and said second stationary pivot axis of said opposing gripping jaws are non-coaxial with respect to one another;
a guide groove and two link pins located on said push element;
a pivot guide recess on each of said first and second gripping jaws proximate each said pivot pin;
a guide pin located in said main body engaging into said guide groove and into the pivot guide recess on each of said first and second gripping jaws;
a pivot link recess on each of said first and second griping jaws located below the respective pivot guide recess, the pivot link recess on each of said first and second gripping jaws engaging with a respective one of said link pins on said push element.

2. The surgical gripping forceps according, to claim 1, wherein said push element links said first and second gripping jaws during said use.

3. The surgical gripping forceps according to claim 1, wherein: said stationary pivot axes of said first and second gripping jaws are parallel to one another.

4. The surgical gripping forceps according to claim 1, wherein: each said first and second stationary pivot axis (61, 71) of respective ones of each said first and second gripping jaws (60, 70) are along a plane that is perpendicularly oriented to said midline of said main body (10).

5. The surgical gripping forceps according to claim 1, further comprising:
each said pivot guide recess providing a bounded opening in respective ones of each of said first and second gripping jaws and having a continuous inner surface;
each said continuous inner surface having at least one curved edge portion; and
said at least one curved edge portion including an arc of a circle defined having a center point of said pivot axis of each respective said pivot pin.

6. A surgical gripping forceps, comprising:
a first gripping jaw and a second gripping jaw that are movable relative to a main body, wherein said first gripping jaw and said second gripping jaw are diametrically opposed to one another, wherein said first gripping jaw has a first stationary pivot axis relative to said main body and a first lever arm, and said second gripping jaw has a second stationary pivot axis relative to said main body and a first lever arm, and a second gripping jaw has a second stationary pivot axis relative to said main body, and a second lever arm, wherein each of said first and second lever arms are articulatable via at least one push element member relative to a defined midline of said main body during a use of said surgical gripping forceps;
a pivot pin on each of said first and second gripping jaws that projects away from respective ones of said first and second gripping jaws,
wherein each said pivot pin of respective ones of said first and second gripping jaws extends along said respective ones of said first and second stationary pivot axes of each respective said first and second gripping jaws and forms said respective pivot axis during said use,
wherein each said pivot pin of said respective first and second gripping jaws that rotates about respective ones of said first and second pivot axes is in a corresponding recess on opposing sides of said main body, and
wherein said first stationary pivot axis and said second stationary pivot axis of said opposing gripping jaws are non-coaxial with respect to one another;
a guide groove and two link pins located air said push element;
a pivot guide recess on each of said first and second gripping jaws proximate each said pivot pin;
a guide pin located in said main body engaging into said guide groove and into the pivot guide recess on each of said first and second gripping jaws;
a pivot link recess on each of said first and second griping jaws located below the respective pivot guide recess, the pivot link recess on each of said first and second gripping jaws engaging with a respective one of said link pins on said push element.

\* \* \* \* \*